(12) United States Patent
Kölbel

(10) Patent No.: US 11,504,130 B2
(45) Date of Patent: Nov. 22, 2022

(54) BALLOON DEVICES AND METHODS FOR USE

(71) Applicant: Tilo Kölbel, Hamburg (DE)

(72) Inventor: Tilo Kölbel, Hamburg (DE)

(*) Notice: Subject to any disclaimer, the term of this patent is extended or adjusted under 35 U.S.C. 154(b) by 487 days.

(21) Appl. No.: 16/570,864

(22) Filed: Sep. 13, 2019

(65) Prior Publication Data
US 2020/0015825 A1    Jan. 16, 2020

Related U.S. Application Data

(63) Continuation of application No. 15/393,195, filed on Dec. 28, 2016, now Pat. No. 10,426,484.

(60) Provisional application No. 62/272,002, filed on Dec. 28, 2015.

(51) Int. Cl.
*A61B 17/12* (2006.01)
*A61M 25/10* (2013.01)

(52) U.S. Cl.
CPC .... *A61B 17/1204* (2013.01); *A61B 17/12109* (2013.01); *A61B 17/12122* (2013.01); *A61M 25/1011* (2013.01); *A61B 2017/1205* (2013.01); *A61B 2017/12127* (2013.01); *A61M 2025/1015* (2013.01); *A61M 2210/125* (2013.01)

(58) Field of Classification Search
CPC .......... A61B 17/1204; A61B 17/12109; A61B 17/12122; A61B 17/12136; A61B 2017/1205; A61B 2017/12127; A61M 25/1011; A61M 2025/1015; A61M 2210/125
See application file for complete search history.

(56) References Cited

U.S. PATENT DOCUMENTS

| | | | | |
|---|---|---|---|---|
| 5,865,789 A | * | 2/1999 | Hattier | A61M 1/1678 604/101.05 |
| 7,766,893 B2 | * | 8/2010 | Thomas | A61M 25/10185 604/509 |
| 2011/0112510 A1 | * | 5/2011 | Stedman | A61K 48/0075 604/509 |
| 2017/0042519 A1 | * | 2/2017 | Sotak | A61B 17/00491 |

* cited by examiner

*Primary Examiner* — Sarah A Simpson
(74) *Attorney, Agent, or Firm* — William A English; Vista IP Law Group LLP

(57) ABSTRACT

Balloon catheters and methods are provided for selectively occluding blood flow into a right atrium of a patient's heart communicating with an inferior vena cava (IVC) and superior vena cava (SVC). In one embodiment, a catheter includes first and second balloons adjacent one another on a distal end of the catheter shaft. During use, the distal end is introduced into the right atrium and positioned such that the first balloon is located within the right atrium. The first balloon is expanded within the right atrium and the catheter shaft directed such that the expanded first balloon engages at least a portion of the IVC to prevent substantial inflow into the right atrium from the IVC. The second balloon is then expanded to limit inflow into the right atrium from the SVC, and a medical procedure is performed within the patient's body.

20 Claims, 6 Drawing Sheets

BALLOON DEVICES AND METHODS FOR USE

RELATED APPLICATION DATA

The present application is a continuation of co-pending application Ser. No. 15/393,195, filed Dec. 28, 2016, issuing as U.S. Pat. No. 10,426,484, which claims benefit of provisional application Ser. No. 62/272,002, filed Dec. 28, 2015, the entire disclosures of which are expressly incorporated by reference herein.

FIELD OF THE INVENTION

The present application relates to balloon devices and methods for using them, and, more particularly, to a double lumen balloon catheter for inflow-occlusion of the inferior and superior vena cava and a method of combining IVC and SVC occlusion for cardiac output reduction.

BACKGROUND

Balloon occlusion in or on top of the inferior vena cava (IVC) is used today to reduce the venous return to the right heart in order to decrease cardiac output during deployment of stent-grafts in the thoracic aorta (TEVAR). This technique is used to reduce the systolic jet of the left ventricle that may displace the graft when partially opened. Thereby, IVC-occlusion improves accurate and precise deployment of stent-grafts. The sudden increase in resistance in the aorta when a stent-graft is opened may also harm the left-ventricular function. This issue is also improved when the reduction of venous return reduces cardiac output by balloon inflation in or on top of the IVC. In TEVAR, the cardiac output reduction achieved by IVC balloon occlusion is sufficient and easily practiced.

Competing techniques of cardiac output reduction during TEVAR include medically induced temporary cardiac arrest by adenosine and rapid ventricular pacing ("RVP"). RVP is a well-established technique to reduce cardiac output during TEVAR, but carries some significant risks and drawbacks.

The drawbacks of RVP include the short period of time during which RVP is tolerated, so deployment needs to be quick, a cardiologist is frequently needed during the procedure, and there are individual differences in compliance. The risks include that the heart may not return to normal rhythm and consequently require CPR and, that the heart ventricles may fill during the RVP due to the continued venous return and thereby expand the ventricle, which may not handle this high volume. The latter may lead to the need for manual cardiac massage to pump out the left ventricular volume. Overall, this problem decreases the applicability of RVP in hearts with decreased pump-function.

Another field where cardiac output reduction is routinely practiced is in trans-catheter aortic valve implantation (TAVI). Here, RVP is used by most cardiologists and cardiac surgeons. In TAVI, the shortcomings of RVP are more frequent than in TEVAR as patients more frequently have a limited left ventricular myocardial function due to structural and coronary heart disease. Most operators find IVC-balloon occlusion in TAVI not applicable, as it does not completely stop cardiac output due to the continued venous return from the superior vena cava (SVC) and the coronary sinus.

A simultaneous balloon-occlusion of the IVC and the SVC would almost completely stop the venous return to the heart and thereby fast and effectively reduce the cardiac output to near zero. Only venous return from the coronary sinus would be left. In contrast to RVP, this technique will not lead to ventricular expansion and therefore reduce the harmful side-effects of cardiac output reduction by RVP.

This maneuver of simultaneously stopping the IVC and SVC return is routinely used in open cardiac surgery, for instance when a side anastomosis of the ascending aorta is opened, to allow slow and controlled filling and reduce strain on the new anastomosis. However, such procedures are not generally used during minimally-invasive procedures.

SUMMARY

The present invention is directed to balloon devices and methods for using them, and, more particularly, to a double-balloon catheter and a method of controlled occlusion of the IVC and the SVC in order to reduce venous return and cardiac output. The devices and methods herein may be used during a variety of medical procedures, particularly during TAVI, TEVAR, and other interventions and operations that may require cardiac output reduction. The devices and methods herein may provide one or more advantages compared to conventional RVP (the most common method used today), such as ease of use, reliability, gentleness, and lower complication rate of CPR and cardiac massage.

In accordance with one embodiment, a balloon catheter is provided for selectively occluding blood flow into a right atrium of a heart communicating with an inferior vena cava (IVC) and superior vena cava (SVC) that includes an elongate shaft comprising a proximal end and a distal end sized for introduction into a patient's body. A first balloon is carried on the distal end formed from compliant or semi-compliant material and having a first length, and a second balloon is carried on the distal end adjacent the first balloon formed from semi-compliant or non-compliant material and having a second length longer than the first length. The first and second balloons are independently expandable, e.g., such that the first balloon may be expanded and engaged with the IVC to prevent substantial inflow from the IVC into the right atrium, and the second balloon may be expanded thereafter to limit inflow from the SVC into the right atrium.

In accordance with another embodiment, a method is provided for selectively occluding blood flow into a right atrium of a patient's heart communicating with an inferior vena cava (IVC) and superior vena cava. A distal end of a catheter shaft may be introduced into the patient's vasculature, the distal end carrying first and second balloons in collapsed conditions, the first balloon formed from compliant or semi-compliant material and having a first length, the second balloon carried on the distal end adjacent the first balloon formed from semi-compliant or non-compliant material and having a second length longer than the first length. The distal end may be advanced into the right atrium, and positioned such that the first balloon is located within the right atrium. The first balloon may be expanded within the right atrium, and the catheter shaft may be directed such that the expanded first balloon engages at least a portion of the IVC to prevent substantial inflow into the right atrium from the IVC. The second balloon may then be expanded such that the second balloon engages at least a portion of the SVC to limit inflow into the right atrium from the SVC, and a medical procedure may be performed within the patient's body.

In accordance with still another embodiment, a balloon catheter is provided for selectively occluding blood flow into a right atrium of a heart communicating with an inferior vena cava (IVC) and superior vena cava that includes an elongate shaft comprising a proximal end, a distal end sized for introduction into a patient's body, and an inflation lumen extending between the first and second ends; and a balloon carried on the distal end comprising a first region having a first length and a second balloon adjacent the first region having a second length longer than the first length, the balloon formed from material such that the second region expands to a preset expanded diameter and the first region expands to a diameter larger than the present expanded diameter.

Other aspects and features of the present invention will become apparent from consideration of the following description taken in conjunction with the accompanying drawings.

BRIEF DESCRIPTION OF THE DRAWINGS

The present invention is best understood from the following detailed description when read in conjunction with the accompanying drawings. It will be appreciated that the exemplary devices shown in the drawings are not necessarily drawn to scale, with emphasis instead being placed on illustrating the various aspects and features of the illustrated embodiments.

DETAILED DESCRIPTION OF THE EXEMPLARY EMBODIMENTS

Figure 1A:
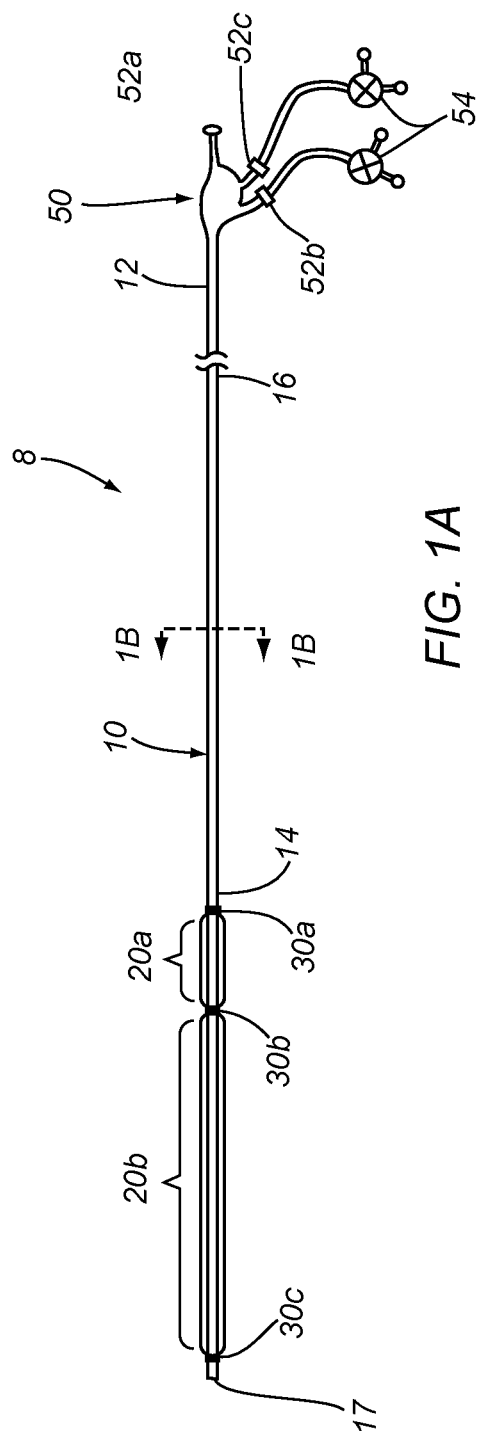
FIG. 1A is a side view of an exemplary embodiment of a double balloon catheter.
Figure 1B:
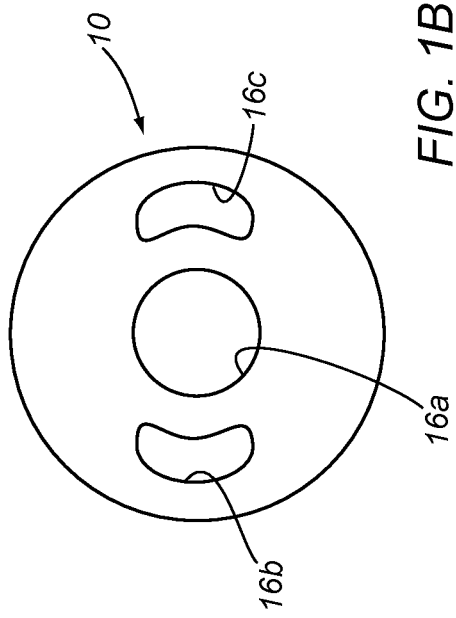
FIG. 1B is a cross-section of the catheter of FIG. 1A taken at 1B-1B.

Turning to the drawings, FIGS. 1A and 1B show an exemplary embodiment of a catheter 8 including a shaft or tubular body 10 including a first or proximal end 12, a second or distal end 14 sized for introduction into a patient's body (not shown), a handle or hub 50 on the proximal end 12, and one or more balloons 20 carried on the distal end 14. For example, as shown in FIG. 1A, first and second balloons 20a, 20b may be provided adjacent one another on the distal end 14 of the shaft 10, e.g., with the first or proximal balloon 20a having a first length that is shorter than a second length of the second or distal balloon 20b.

In addition, the shaft 10 includes one or more lumens 16 extending at least partially between the proximal and distal ends 12, 14. For example, a central or instrument lumen 16a may extend from a first port 52a in the hub 50 through the shaft 10 to a distal or outlet port 17, which may be sized to receive one or more instruments, e.g., a guidewire or other rail (not shown). Optionally, the first port 52a may include one or more seals, e.g., a hemostatic valve (also not shown), which may provide a substantially fluid-tight seal, while accommodating insertion of one or more instruments or fluids into the instrument lumen 16a. Optionally, a side port (not shown) may be provided on the hub 50 that communicates with the instrument lumen 16a, e.g., for delivering fluid into and/or aspirating fluid from the instrument lumen 16a, e.g., around an instrument inserted into the instrument lumen 16a. In yet another option, the instrument lumen 16a may include lubricious material or may include one or more coatings on the inner surface thereof having desired properties, e.g., a lubricious coating, to reduce friction and/or otherwise facilitate introducing an instrument through the instrument lumen 16a.

In addition, the shaft 10 may include one or more inflation lumens communicating with the interiors of the balloons 20, e.g., a first inflation lumen 16b communicating between a second port 52b on the hub 50 and the interior of the first balloon 20a and a second inflation lumen 16c communicating between a third port 52c on the hub 50 and the interior of the second balloon 20b. As shown in FIG. 1B, the inflation lumens 16b, 16c may be provided opposite one another around the instrument lumen 16a. Alternatively, the lumens 16 may be provided in other configurations or positions, which may remain the same or may vary along the length of the shaft 10, as desired. Generally, the instrument lumen 16a will be larger than the inflation lumens 16b, 16c, e.g., sized to accommodate a 0.0035 inch guidewire.

As shown in FIG. 1A, the second and third ports 52b, 52c may include one or more connectors 54b, 54c, e.g., a male or female Luer fitting, a stop-cock, and the like, which may allow a source of inflation media and/or aspiration (also not shown) to be coupled to the ports 52b, 52c and/may selectively allow access and/or isolate the inflation lumens 20b, 20c. For example, a syringe carrying saline or other fluid (not shown) may be coupled to each of the ports 52b, 52c (e.g., two syringes simultaneously, or one syringe separately) such that a plunger of the syringe may be selectively advanced to direct fluid through the corresponding inflation lumen 16b, 16c to inflate the corresponding balloon 20a, 20b, and/or may be withdrawn to remove the fluid from within the corresponding balloon 20a, 20b to deflate the balloon 20a, 20b. Thus, in this embodiment, the balloons 20a, 20b may be expandable independently of one another, e.g., as described further elsewhere herein.

The shaft 10 may have a length sufficient to extend from a location outside a patient's body, e.g., a percutaneous entry site, into the patient's vasculature, e.g., such that the distal end 14 may be introduced into or adjacent a heart 90 (not shown, see, e.g., FIGS. 2-6), as described elsewhere herein. An exemplary length of the shaft 10 may be at least about eighty centimeters (80 cm), e.g., sufficiently long to allow introduction from the femoral veins into the vena cava 92, 96 (not shown, see, e.g., FIGS. 2-6).

The shaft 10 may have a substantially uniform construction and size along its length between the proximal and distal ends 12, 14. Alternatively, the mechanical properties and/or geometry of the shaft 10 may vary along its length. For example, a distal end 14 of the shaft 10 may be substantially flexible to facilitate advancement through tortuous anatomy, while the proximal end 12 may be semi-rigid or rigid to enhance pushability and/or torqueability of the shaft 10 without substantial risk of buckling or kinking. Optionally, a distal portion of the shaft 10 underlying the balloons 20a, 20b may have variable construction along its length, e.g., being more rigid beneath and/or between the balloons 20a, 20b to maintain balloon spacing and/or otherwise facilitate manipulation of the catheter 8 in a desired manner.

With continued reference to FIG. 1A, the first balloon 20a may have a length that is shorter than the second balloon 20b. In an exemplary embodiment, the first balloon 20a may be formed from compliant and/or elastic material, e.g., such that the size of the first balloon 20a may vary proportionally to the volume of fluid introduced into its interior and/or to facilitate the first balloon 20a changing shape, e.g., to conform to surrounding anatomy, as described further below. In an exemplary embodiment, the first balloon 20a may expand to a diameter of at least about fifty millimeters (50 mm) and may have a length of not more than about four centimeters (4 cm).

In contrast, the second balloon 20b may be relatively long compared to the first balloon 20a, e.g., sized to inflate to a diameter between about twenty to forty millimeters (20-40 mm) and having a length between about eight and fifteen centimeters (8-15 cm). The second balloon 20b may be formed from compliant or semi-compliant material, e.g., which may limit the size of the second balloon 20b and/or allow some conformance to surrounding anatomy. Generally, the second balloon 20b is configured to be inflated after inflating the first balloon 20a, e.g., such that at least a portion of the second balloon 20b sits on or otherwise overlies, abuts, or contacts at least a portion of the inflated first balloon 20a, as described further elsewhere herein. Optionally, the material of the shaft 10 may be relatively stiffer in the area of the balloons 20a, 20b than other sections of the shaft 10, e.g., to prevent proximal migration of the second balloon 20b, e.g., towards or under the proximal balloon 20a.

In an alternative embodiment, instead of a single balloon for the second or distal balloon 20b, a pair of concentric balloons (not shown) may be provided, e.g., with inner and outer balloons having lengths similar to that shown for the second balloon 20b. The inner and outer balloons may communicate with separate inflation lumens (also not shown) such that the inner and outer balloons may be expanded independently of one another. For example, the outer balloon may be formed from compliant or semi-compliant material while the inner balloon may be formed from noncompliant material. In this manner, the inner balloon may be inflated initially, which may cause the inner balloon to be expanded to a preset expanded diameter and/or shape given its noncompliant material and the outer balloon may be inflated thereafter to expand outwardly from the expanded diameter of the inner balloon, which may enhance engagement and/or sealing, as described elsewhere herein.

Optionally, as shown in FIG. 1A, the shaft 10 and/or the balloons 20a, 20b may include one or more markers 30, e.g., bands of radiopaque material, cinched, deposited, secured, or otherwise applied around the shaft 10 at desired locations, e.g., to facilitate identifying the proximal and distal ends of the balloons 20a, 20b using external imaging, such as fluoroscopy. In the exemplary embodiment shown, a first marker 30a may be provided at the proximal end of the first balloon 20a, a second marker 30b may be provided between the balloons 20a, 20b, and a third marker 30c may be provided at the distal end of the second balloon 20b.

Figure 2:
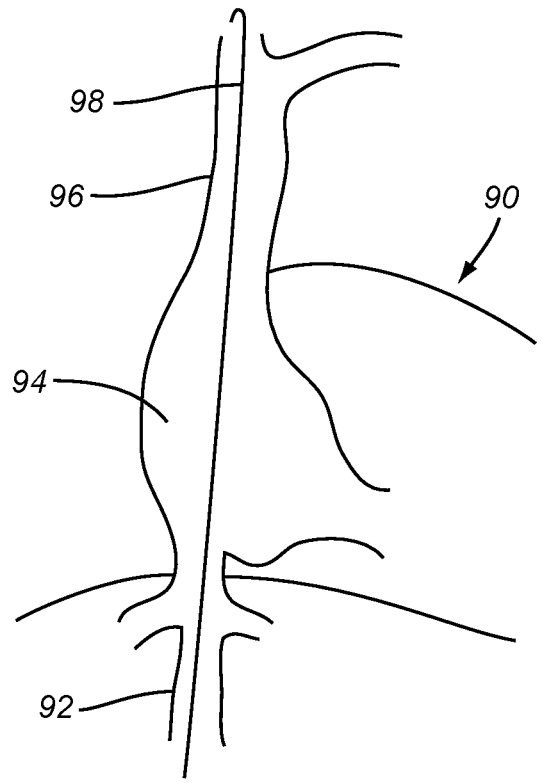
FIGS. 2-6 are cross-sectional views of a patient's body showing an exemplary method for using a catheter, such as the catheter of FIG. 1A, to perform a procedure, e.g., within the right atrium and the vena cava.

Turning to FIGS. 2-6, an exemplary method for using the catheter 8 of FIG. 1A is shown, e.g., to isolate the inferior vena cava ("IVC") 92 and/or superior vena cava 96 ("SVC") communicating with the right atrium 94 of a patient's heart 90. Initially, the vasculature of the patient may be accessed, e.g., after puncture of the femoral vein or other access site within the venous system, and a guidewire 98 may be introduced into the patient's vasculature, e.g., through the iliac veins, the IVC 92, the right atrium 94, and into the SVC 96. Optionally, a tip of the guidewire 98 may be advanced further, e.g., into the jugular vein as shown in FIG. 2.

Figure 3:
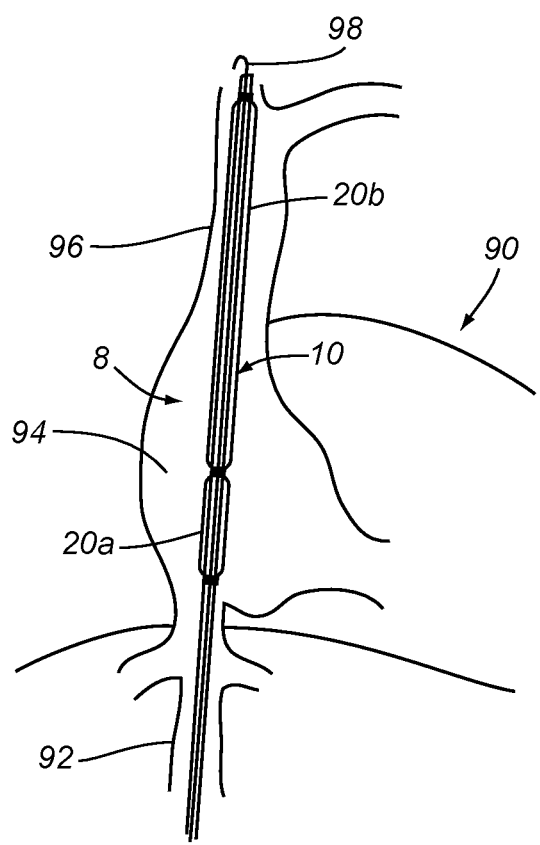

Once the guidewire 98 is properly positioned, the distal end 14 of the shaft 10 (with the balloons 20a, 20b in collapsed conditions) may be advanced over the guidewire 98, e.g., alone or in combination with an access sheath (not shown). For example, the distal end 14 may be advanced over the guidewire 98 through the IVC 92 into the right atrium 94 such that the first balloon 20a is advanced and positioned within the right atrium 94, e.g., as shown in FIG. 3.

Figure 4:
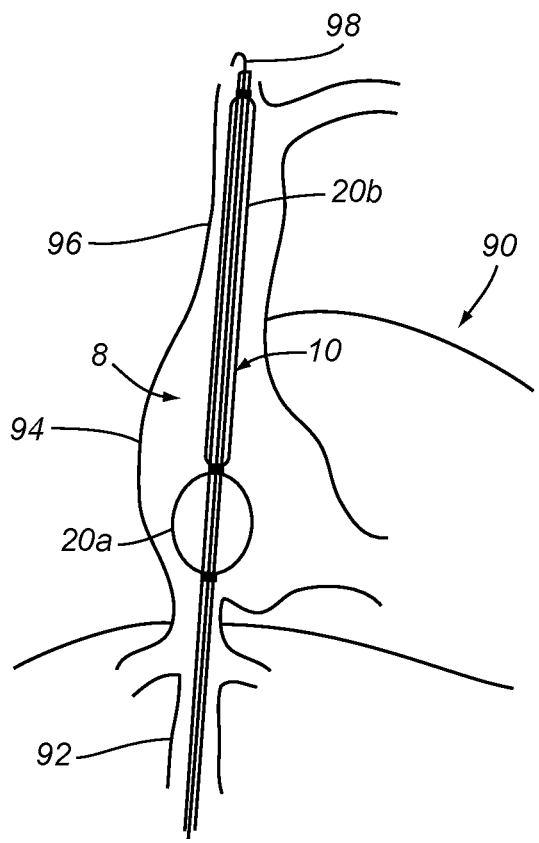

The first balloon 20a may then be inflated, e.g., via a source of fluid, such as a syringe (not shown) coupled to the second port 52b. In an exemplary embodiment, the first balloon 20a may be configured to fully expand upon receiving between about thirty and fifty milliliters (30-50 ml) of saline within its interior, thereby expanding the first balloon 20a to an expanded condition, e.g., to a diameter of about forty millimeters (40 mm). With the first balloon 20a exposed within the right atrium 94, the first balloon 20a may expand to a substantially spherical shape given its compliance, e.g., as shown in FIG. 4.

Figure 5:
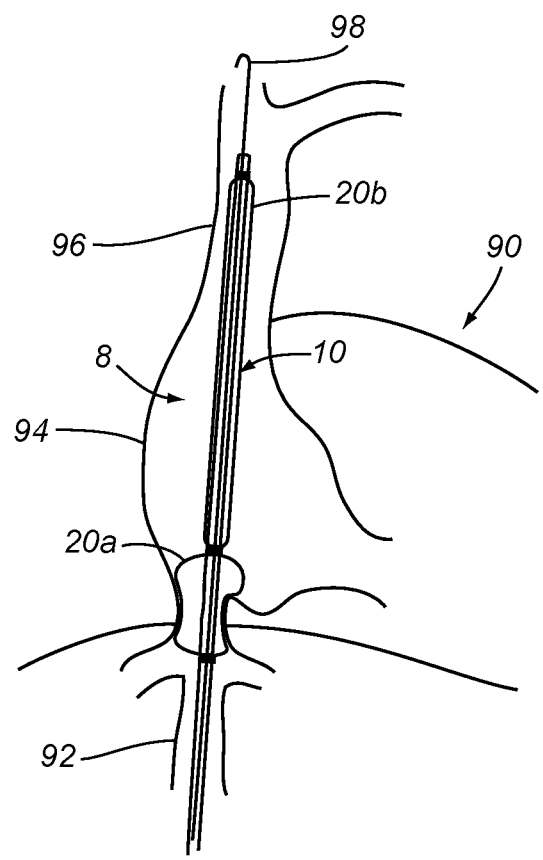

The catheter 8 may then be partially withdrawn, e.g., to pull the expanded first balloon 20a proximally until it engages and/or is received at least partially within the IVC 12, as shown in FIG. 5. As shown, the first balloon 20a may conform to the outlet of the IVC 92 and/or otherwise deform elastically to provide a substantially fluid-tight seal, thereby occluding inflow of the IVC 92 into the right atrium 94, e.g., at the level of the diaphragm. Proximal tension may be maintained on the shaft 10, e.g., manually or using an external device engaging the hub 50 of the catheter 8 (not shown), to maintain the seal.

Figure 6:
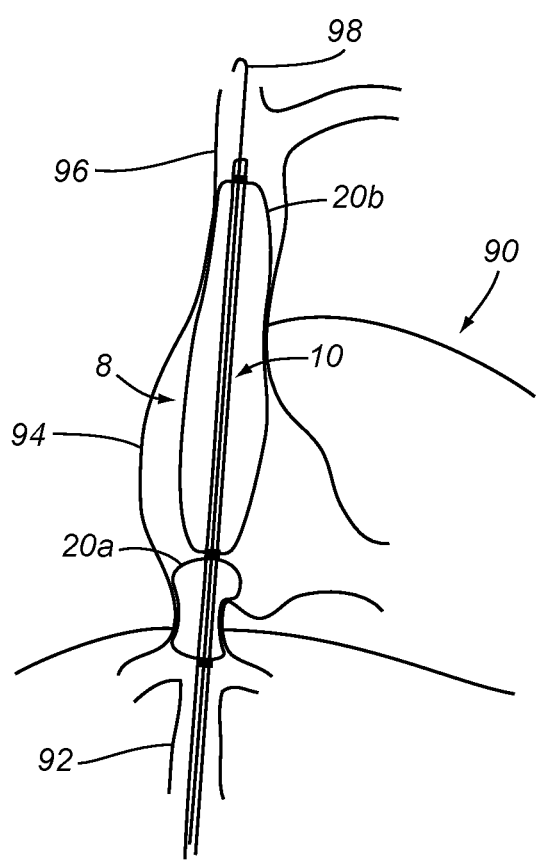

Turning to FIG. 6, the distal balloon 20b may then be inflated, e.g., via a source of fluid, such as a syringe (not shown) coupled to the third port 52c. Given its length, the second balloon 20b may expand to at least partially occlude the SVC 94, e.g., to an extent that provides the desired cardiac output reduction.

Alternatively, as described above, instead of a single balloon for the distal balloon 20b, a pair of concentric distal balloons (not shown) may be provided, e.g., having a length similar to the distal balloon 20b. For example, the outer balloon may be formed from compliant or semi-compliant material while the inner balloon may be formed from noncompliant material. Consequently, instead of a single expansion of the distal balloon 20b, the inner distal balloon may be inflated initially, which may cause the inner balloon to be expanded to a preset expanded diameter and/or shape given its noncompliant material. For example, the expanded diameter may be selected to correspond generally to the diameter of the SVC 96, e.g., to at least partially occlude the SVC 96 when expanded. For example, the inner balloon may slow but not completely stop inflow into the right atrium 94 from the SVC 96.

Thereafter, the outer distal balloon may be inflated, e.g., to expand outwardly from the expanded diameter of the inner balloon. Given the compliant or semi-compliant nature of the outer balloon, the outer balloon may conform the surrounding anatomy and/or enhance engagement, e.g., with the SVC 96, to enhance occlusion of the SVC 96. Thus, the outer balloon may be selectively expanded and/or collapsed with the inner balloon expanded, as desired, to controllably obstruct inflow from the SVC 96.

When a desired pressure curve is achieved, e.g., without a systolic jet, one or more procedures may be performed within the patient's heart, vasculature, and/or other locations within the patient's body. For example, as explained above, a TAVI or TEVAR procedure may then be undertaken with the IVC 92 and SVC 96 substantially sealed, e.g., to prevent fluid accumulation within chambers of the heart 90 and/or in other tissues. After the procedure is completed, the second balloon 20b may be deflated first and then the tension may be released from the first balloon 20a. The first balloon 20a may then be deflated and the catheter 8 and guidewire 98 removed from the patient's body using conventional methods.

Figure 7A:
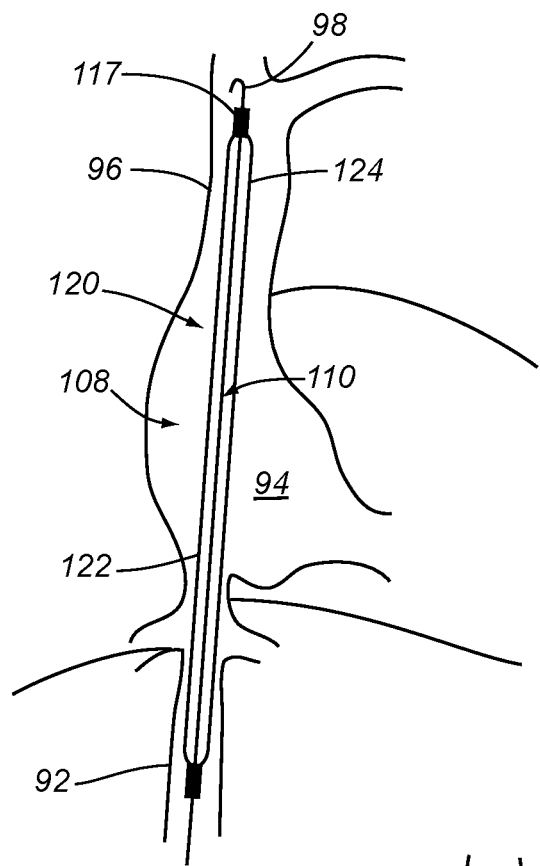
FIGS. 7A-7C are cross-sectional views of a patient's body showing an exemplary method for using a catheter including a single elongate balloon to selectively isolate the superior and inferior vena cava from the right atrium.
Figure 7B:
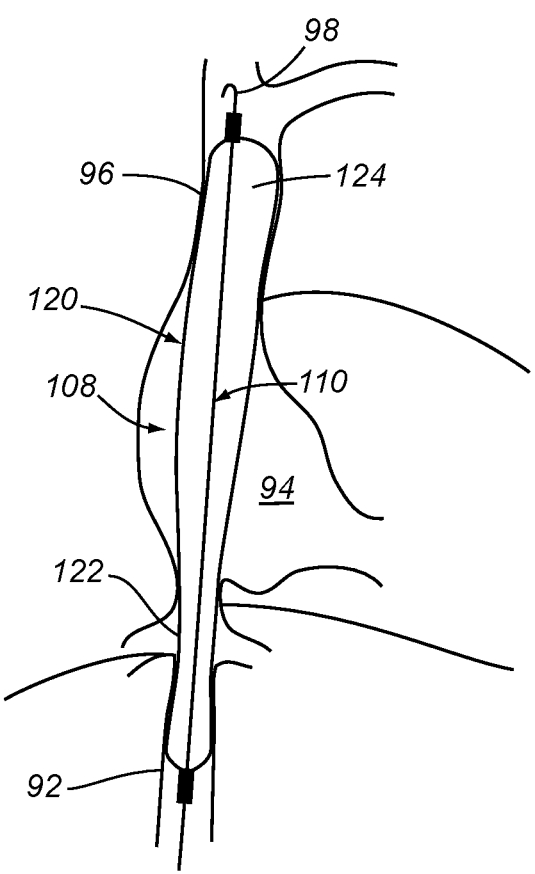
Figure 7C:
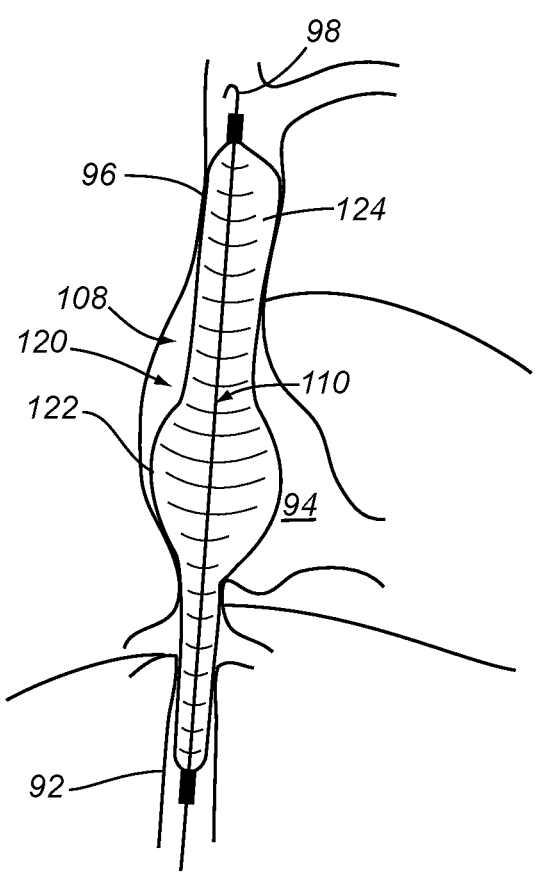

Alternatively, as shown in FIGS. 7A-7C, a catheter 108 may be used that includes a single balloon having different regions for selectively occluding the IVC 92 and/or SVC 96. Generally, the catheter 108 includes a shaft 110 including a first or proximal end (not shown), a second or distal end 114 sized for introduction into a patient's body, similar to the previous embodiment. However, instead of two balloons, the distal end 114 of the shaft 110 carries only a single relatively long balloon 120 having different regions, e.g., a first or proximal region 122 and a second or distal region 124 that correspond generally to the proximal and distal balloons 20a, 20b of the previous embodiment. For example, the proximal region 122 may be relatively shorter than the distal region 124. In addition, or alternatively, the balloon 122 may be constructed from material such that the proximal region 122 expands to a larger diameter and/or other cross-section than the distal region 124.

For example, the thickness of the balloon 120 may be varied between the proximal and distal regions 122, 124, e.g., with the wall of the distal region 124 being thicker than the wall of the proximal region 122. In addition or alternatively, the distal region 124 may be formed from a relatively higher Durometer material than the proximal region 122. Further, in addition or alternatively, the wall of the balloon 120 may be reinforced more along the distal region 124 than the proximal region 122 to allow the proximal region 122 to expand greater than the distal region 124.

In addition, the shaft 110 includes one or more lumens, e.g., an instrument lumen (not shown) extending between a port in a handle or hub (not shown) and an opening 117 in the distal end 114, e.g., sized for receiving a guidewire 98 therethrough, similar to the previous embodiment. In addition, the shaft 110 may include an inflation lumen communicating with an interior of the balloon 120. Thus, in this alternative, both regions 122, 124 of the balloon 120 may expand substantially simultaneously as the balloon 120 is inflated.

Turning to FIG. 7A, during use, with the balloon 120 collapsed, the distal end 114 of the catheter 108 may be introduced into the patient's body, e.g., over a guidewire 98 previously placed to extend from a percutaneous entry site into the patient's heart 90, e.g., through the IVC 92 and right atrium 94 into the SVC 96, as described previously. For example, the guidewire 98 may be back-loaded through the opening 117 into the instrument lumen, and the shaft 110 may be advanced over the guidewire 98 until the balloon 120 is positioned within the heart 90, e.g., with the proximal region 122 adjacent the IVC 92 and the distal region 124 extending through the right atrium 94 into the SVC 96.

As shown in FIGS. 7B and 7C, the balloon 120 may be inflated and the shaft 110 manipulated, as needed, to isolate the IVC 92 and/or SVC 96, similar to the previous embodiments. Unlike the previous embodiment, since a single balloon is provided, both regions 122, 124 may expand substantially simultaneously. Alternatively, if the distal region 124 is constructed to resist expansion more than the proximal region 122, during inflation, the proximal region 122 may inflate first to allow the IVC 92 to be selectively occluded before fully expanding the balloon 120 and the distal region 124. Once the IVC 92 and SVC 96 are sufficiently sealed, one or more procedures may be performed, similar to the methods described above.

It will be appreciated that the devices and methods described herein may be used in minimally-invasive, e.g., catheter-based procedures, as well as open surgical procedures.

Optionally, the orientation of the balloons 20a, 20b and/or regions 122, 124 may be reversed on the shaft 10, 110, if desired. For example, if groin access, jugular access, or other similar access sites are used, the configuration of the proximal and distal balloons would be reversed to allow the IVC 92 to be selectively isolated first before at least partially sealing the SVC 96.

In yet another option, the shaft may include one or more additional lumens and/or may carry one or more additional balloons (not shown) communicating with the respective lumens, e.g., to provide additional functionality to the catheter.

In still another option, an inner channel may be provided on the shaft that may be opened and closed from outside the patient's body. This may allow inflation of both balloons and occluding IVC and SVC first (longer maneuver) and then more accurately occlude or open venous return by the handle.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A method for selectively occluding blood flow into a right atrium of a patient's heart communicating with an inferior vena cava (IVC) and superior vena cava (SVC), comprising:

introducing a distal end of a catheter shaft into the patient's vasculature, the distal end carrying a balloon in a collapsed condition, the balloon comprising a proximal region and a distal region adjacent the proximal region, the proximal region formed from compliant or semi-compliant material and having a first length, the distal region formed from semi-compliant or non-compliant material and having a second length longer than the first length;

advancing the distal end into the right atrium;

positioning the distal end such that the proximal region is located within the right atrium;

inflating the balloon to expand the proximal region within the right atrium while the distal region remains substantially collapsed;

directing the catheter shaft such that the expanded proximal region engages at least a portion of the IVC to prevent substantial inflow into the right atrium from the IVC;

further inflating the balloon to expand the distal region such that the distal region engages at least a portion of the SVC to limit inflow into the right atrium from the SVC; and performing a medical procedure within the patient's body.

2. The method of claim 1, wherein the distal end of the catheter shaft is advanced into the right atrium from the IVC such that the distal region at least partially enters the SVC.

3. The method of claim 1, wherein, when directing the catheter shaft such that the expanded proximal region engages at least a portion of the IVC, at least a portion of the distal region remains within the SVC.

4. The method of claim 1, wherein the proximal region expands to a substantially spherical shape when expanded within the right atrium, and wherein the proximal region at least partially enters the IVC when the catheter shaft is withdrawn such that the proximal region is deformed from the substantially spherical shape to enhance sealing of the IVC.

5. The method of claim 1, further comprising, upon completing the medical procedure:
deflating the balloon back to the collapsed condition; and
removing the catheter shaft from the patient's body.

6. The method of claim 1, wherein the distal region is expanded for sufficient time to reduce cardiac output in a desired manner.

7. The method of claim 1, further comprising monitoring pressure within the patient's heart to achieve a desired pressure curve before performing the medical procedure.

8. The method of claim 7, further comprising selectively deflating and inflating the distal region to modify inflow into the right atrium from the SVC to achieve the desired pressure curve.

9. The method of claim 1, wherein the medical procedure comprises implantation of a trans-catheter aortic valve.

10. A method for selectively occluding blood flow into a right atrium of a patient's heart communicating with an inferior vena cava (IVC) and superior vena cava (SVC), comprising:
introducing a distal end of a catheter shaft into the patient's vasculature, the distal end carrying a balloon in a collapsed condition, the balloon comprising a proximal region and a distal region adjacent the proximal region, the proximal region formed from compliant or semi-compliant material and having a first length, the distal region formed from semi-compliant or non-compliant material and having a second length;
advancing the distal end into the right atrium;
positioning the distal end such that the proximal region is located within the right atrium;
inflating the balloon to expand the proximal region within the right atrium while the distal region remains substantially collapsed;
directing the catheter shaft such that the expanded proximal region engages at least a portion of the IVC to prevent substantial inflow into the right atrium from the IVC;
further inflating the balloon to expand the distal region such that the distal region engages at least a portion of the SVC to limit inflow into the right atrium from the SVC; and
performing a medical procedure within the patient's body.

11. The method of claim 10, wherein the distal end of the catheter shaft is advanced into the right atrium from the IVC such that the distal region at least partially enters the SVC.

12. The method of claim 10, wherein, when directing the catheter shaft such that the expanded proximal region engages at least a portion of the IVC, at least a portion of the distal region remains within the SVC.

13. The method of claim 10, wherein the proximal region expands to a substantially spherical shape when expanded within the right atrium, and wherein the proximal region at least partially enters the IVC when the catheter shaft is withdrawn such that the proximal region is deformed from the substantially spherical shape to enhance sealing of the IVC.

14. The method of claim 10, further comprising, upon completing the medical procedure:
deflating the balloon back to the collapsed condition; and
removing the catheter shaft from the patient's body.

15. The method of claim 10, wherein the distal region is expanded for sufficient time to reduce cardiac output in a desired manner.

16. The method of claim 10, further comprising monitoring pressure within the patient's heart to achieve a desired pressure curve before performing the medical procedure.

17. The method of claim 16, further comprising selectively deflating and inflating the distal region to modify inflow into the right atrium from the SVC to achieve the desired pressure curve.

18. The method of claim 10, wherein the medical procedure comprises implantation of a heart valve.

19. The method of claim 10, wherein the medical procedure comprises one of a TAVI or a TEVAR procedure.

20. The method of claim 10, wherein the first length is shorter than the second length.

* * * * *